United States Patent [19]

Nagata

[11] Patent Number: 4,950,378
[45] Date of Patent: Aug. 21, 1990

[54] BIOSENSOR

[75] Inventor: Yasuhiro Nagata, Kusatsu, Japan

[73] Assignee: Daikin Industries, Ltd., Osaka, Japan

[21] Appl. No.: 215,804

[22] Filed: Jul. 6, 1988

[30] Foreign Application Priority Data

Jul. 17, 1987 [JP] Japan .................. 62-179814

[51] Int. Cl.$^5$ .......................... G01N 27/327
[52] U.S. Cl. .................. 204/402; 204/403;
                        204/406; 204/412; 204/415
[58] Field of Search ............ 204/1 T, 1 E, 1 P, 402,
                        204/403, 415, 412, 406

[56] References Cited

U.S. PATENT DOCUMENTS

| 4,077,861 | 3/1978 | Lauer ........................ 204/402 |
| 4,505,784 | 3/1985 | Mund et al. ................ 204/402 |
| 4,566,949 | 1/1986 | Berger ....................... 204/402 |
| 4,705,617 | 11/1987 | Beebe et al. .............. 204/402 |
| 4,772,375 | 9/1988 | Wullschleger et al. ...... 204/402 |

FOREIGN PATENT DOCUMENTS

| 60-155959 | 8/1985 | Japan . |
| 1531761 | 11/1978 | United Kingdom ......... 204/402 |

Primary Examiner—T. Tung
Attorney, Agent, or Firm—Wenderoth, Lind & Ponack

[57] ABSTRACT

An electrode refreshing arrangement of a biosensor includes a constant reverse bias voltage arranged to be supplied between a working electrode and a reference electrode, so as to thereby refresh the working electrode, that is, to remove the disturbance film or substance formed on the surface of the working electrode as a result of the enzyme reaction, thus reviving the activity of the working electrode.

8 Claims, 2 Drawing Sheets

Fig. 3
Fig. 1
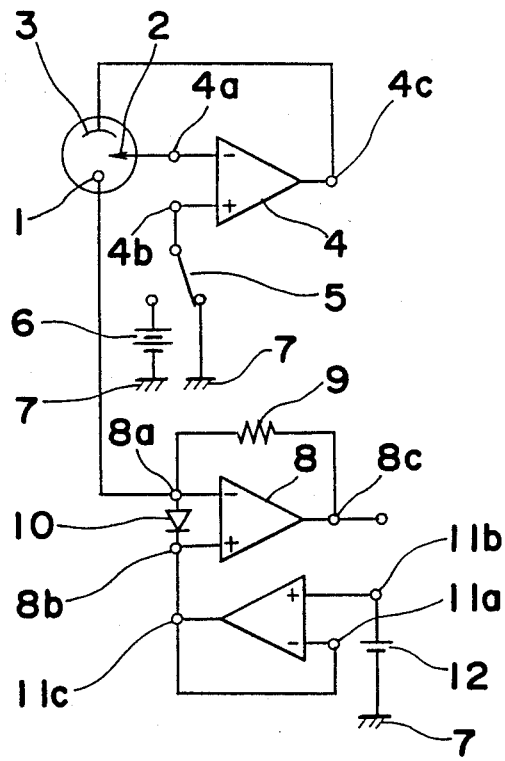
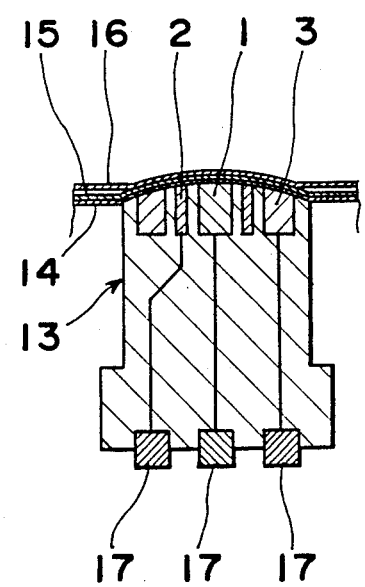
Fig. 4
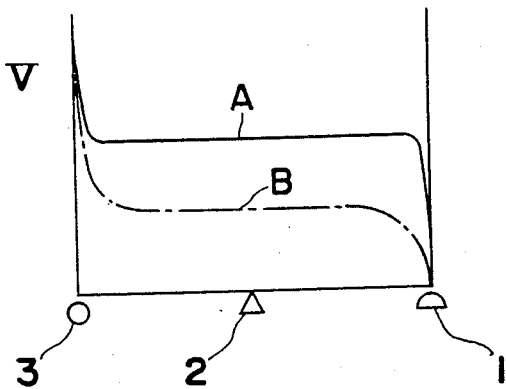

BIOSENSOR

BACKGROUND OF THE INVENTION

The present invention generally relates to a biosensor and, more particularly, to a biosensor provided with an electrode refreshing arrangement which is arranged to apply to an electrode of the biosensor a bias voltage having opposite polarity to that at the time of measurement, before starting the measurement.

Conventionally, a biosensor has attracted attention to the characteristics thereof in that it can detect considerably complicated organic compounds, etc. with a high sensitivity and with a high selectivity, and studies have been extended to various kinds of such biosensors.

For a representative of such a biosensor as referred to above, it has been proposed to detect the presence or absence of a substance, or the amount of a substance present in an object to be measured on the basis of an electrical signal output from an electrode which is secured with physiologically active material, and applied which is supplied with a predetermined normal bias voltage; for example, it has been proposed that $H_2O_2$ generated as a result of the reaction between an enzyme secured to an enzyme film and an object to be measured is arranged to be led to the surface of an electrode through an $H_2O_2$ transmissive film, with a working electrode and a counter electrode made of Pt, so that an electrical signal corresponding to the amount of $H_2O_2$ penetrating the film is output to detect the presence or absence of a substance in the object to be measured or the amount of the substance present in the object. Concretely speaking, the working electrode is given a 0.6 V normal bias voltage with respect to the standard counter electrode.

According to the above-described biosensor, when the measurement of the object is continuously carried out in the state where the working electrode is supplied with normal bias voltage, a disturbance film against the circulation of electricity such as an oxide film is disadvantageously formed on the surface of the working electrode, deteriorating the activity of the working electrode. Therefore, for solving this problem, it has also been proposed, as disclosed in the published specification of Japanese Pat. Publication (unexamined) No. 60-155959, that after several measurement operations have been conducted, a reverse bias voltage is supplied to the working electrode while the measurement is not carried out, that is, about −0.6 V is added to the working electrode in the above-described example, so as to thereby remove the disturbance film and revive the activity of the working electrode, so that the output signal is returned to its original level.

Thus, in the manner as above, the deteriorated measuring sensitivity of the electrode can be restored by the application of the predetermined reverse bias voltage to the working electrode when the measurement is not carried out and, the measurement can be performed with a high sensitivity again.

However, according to the above-described prior art, the voltage drop (referred to as an overvoltage hereinafter) in the counter electrode is changed by the flowing current since a constant voltage is applied for refreshing use between the working electrode and the counter electrode, resulting in the change of the voltage applied to the working electrode. Accordingly, it is not certain that constant refreshing effect can always be achieved, namely, the activity restoration of the working electrode can always be realized. Since the change of the refreshing effect will change the activity condition of the working electrode after the refreshing thereof, the level of the output electrode signal is unfavorably changed.

In addition, while the refreshing operation is being done, a current which is approximately ten times the current during the time of measurement flows, which necessitates a larger area for the counter electrode. Therefore, the arrangement as a whole is inevitably bulky, with an increase in its manufacturing cost.

Referring to FIG. 7, there is shown a circuit diagram of a prior art bias supplying arrangement in a biosensor which is provided with a reference electrode 26 in addition to a working electrode 24 and a counter electrode 27. In the bias supplying arrangement of FIG. 7, a direct current source 21 is connected for measurement use between a non-inverting input terminal of an operational amplifier 23 and ground, and moreover, a resistance 22 for current-voltage conversion use is connected between an inverting input terminal and an output terminal of the operational amplifier 23. The working electrode 24 is connected to the inverting input terminal of the operational amplifier 23. An operational amplifier 25 which has its non-inverting input terminal connected to ground has its inverting input terminal connected to the reference electrode 26 and its output terminal connected to the counter electrode 27.

Employing the above construction, even when the counter electrode 27 is not so large, if the potential difference between the working electrode 24 and the reference electrode 26 is continued to be held constant, the counter electrode 27 is able to be rid of the influences of the overvoltage and thus a correct measurement can be obtained.

As shown in FIG. 5, in the construction of FIG. 7, since the level of the output signal, as shown with a chain line B, is not stable before considerable time has passed after supply of electricity, the measurement is generally started after sufficient time for stabilization of the level of the output signal has passed (approximately one hour at the longest), and moreover, it is arranged to shorten the time required before the subsequent measurement by maintaining the state where the electricity is always supplied once after the supply thereof.

However, the stabilized level of the output signal is much lower than the level of the output signal at the initial stage of the supply of electricity, and therefore the resolution is deteriorated. Moreover, if the supply of electricity is interrupted or the battery is cut off halfway through a measurement, it takes a long time before the level of the output signal is returned to be stable after the supply of electricity resumes.

SUMMARY OF THE INVENTION

Accordingly, an essential object of the present invention is to provide a biosensor which is arranged to measure the density of an objective material with high accuracy on the basis of an electrical signal generated under the given conditions, with eliminating the above-described disadvantages inherent in the prior art.

Another object of the present invention is to provide an electrode refreshing arrangement for a biosensor which is provided with a reference electrode to achieve a counter electrode which is compact, and at the same time, which is arranged to enable the immediate start of a measurement after the supply of electricity, with an improved measuring resolution.

In accomplishing the above-described objects, according to the present invention, the electrode refreshing arrangement is comprised of a first constant voltage supplying means for supplying constant voltage between a working electrode and a reference electrode for the purpose of refreshing the working electrode, a second constant voltage for the purpose of measurement, and a selecting means for selecting, when the measurement is carried out, the state where the constant voltage is supplied by the first constant voltage supplying means for the purpose of refreshing, and the state where the constant voltage is supplied by the second constant voltage supplying means for the purpose of measurement, alternately in this order.

It is to be noted here that the above-mentioned selection means is preferably such that it selects the first state where the constant voltage is supplied by the first constant voltage supplying means for the purpose of refreshing for a relatively short period of time and then selects the second state where the constant voltage is supplied by the second constant voltage supplying means for the purpose of measurement.

It is also preferable for the construction of the above first constant voltage supplying means and the second constant voltage supplying means and the selecting means that a non-inverting input terminal of an operational amplifier which has its output terminal connected to the counter electrode and its inverting input terminal connected to the reference electrode is selectively connected by a switch to an output terminal of the refreshing direct current source and to ground.

Moreover, it is preferable for the above-described reference electrode to be made of Ag.

In the electrode refreshing arrangement having the above-described construction, before starting of the actual measurement, the selecting means selects the state where the constant voltage is supplied for refreshing by the first voltage supplying means, so that the constant voltage for refreshing is supplied between the working electrode and the reference electrode, thereby refreshing the working electrode, or in other words, removing the disturbance substance. Then, after refreshing the working electrode, the selecting means selects the state where the constant voltage for measurement is supplied by the second voltage supplying means. Consequently, the constant voltage is supplied between the working electrode and the reference electrode for measurement, bringing the normal bias condition. Accordingly, in the condition as above, an electrical signal corresponding to the amount of material produced or lost by the reaction of the object to be measured with the physiologically active material is generated between the working electrode and the counter electrode, and on the basis of such a signal, the density of the object to be measured can be detected.

More specifically, the above-described refreshing operation is to remove the disturbance substance formed on the surface of the working electrode. When the inventors of the present invention studied the operation for removing the disturbance substance, it was found that the operation for removing the disturbance substance was carried out depending on the supplied current. Therefore, if the constant voltage is continuously supplied between the working electrode and the counter electrode for refreshing, it is the same thing as if the sum of the voltage drop in the vicinity of the surface of the working electrode and the voltage drop in the vicinity of the surface of the counter electrode is kept constant, and the voltage drop in the vicinity of the surface of the working electrode which is necessary for arousing the refreshing effect is not held constant. As a result of this, the refreshing effect can not be maintained constant, and the activity of the working electrode after refreshing is disturbed, whereby the measurement accuracy after refreshing is not improved much. On the contrary, according to the present invention, since it is so arranged that the working electrode is refreshed while the voltage applied between the working electrode and the reference electrode is kept constant, the voltage drop in the vicinity of the surface of the working electrode can be kept constant. Therefore, the current value when removing the disturbance substance can be held substantially constant, thereby realizing an effective refreshing of the working electrode in a short period of time.

After the refreshing of the working electrode is completed, the selection means selects the state where the constant voltage is supplied for measurement by the second constant voltage means, so that the constant voltage for measurement is supplied between the working electrode and the reference electrode, bringing the arrangement in the normal bias condition. Since the activity of the working electrode is sufficiently increased in the above-described normal bias condition, the output signal is in high level and the measuring resolution is high.

In the case where the selecting means selects the state where the constant voltage for refreshing is supplied for a relatively short period of time, and then selects the state where the constant voltage for measurement is supplied, the working electrode is activated enough only by a relatively short time refreshing operation, thus reducing, on a large scale, the time required before starting the measurement.

Furthermore, in the case where the first constant voltage supplying means for refreshing, the second constant voltage supplying means for measurement and the selecting means are constructed in such a manner that the non-inverting input terminal of the operational amplifier which has its output terminal connected to the counter electrode and has its inverting input terminal connected to the reference electrode is selectively connected to the output terminal of the direct current source for refreshing or to ground by a switch, most parts of the arrangement can be made common, resulting in a simplified structure of the arrangement as a whole.

In addition, when the reference electrode is made of Ag, the surface potential of the reference electrode can be retained constant, so that the surface potential of the working electrode can be positively maintained by the refreshing constant voltage between the working electrode and the reference electrode, thereby achieving stable refreshing effects.

BRIEF DESCRIPTION OF THE DRAWINGS

These and other objects and features of the present invention will become clear from the following description taken in conjunction with the preferred embodiments thereof with reference to the accompanying drawings, in which:

FIG. 1 is a cross-sectional view showing an enzyme electrode body of a biosensor according to one preferred embodiment of the present invention;

FIG. 3 is a circuit diagram of a control circuit connected to the body to provide the biosensor of FIG. 1;

FIG. 4 is a graph showing changes of voltage to be measured at the position electrodes of the biosensor of FIG. 1;

DETAILED DESCRIPTION OF THE INVENTION

Figure 7:
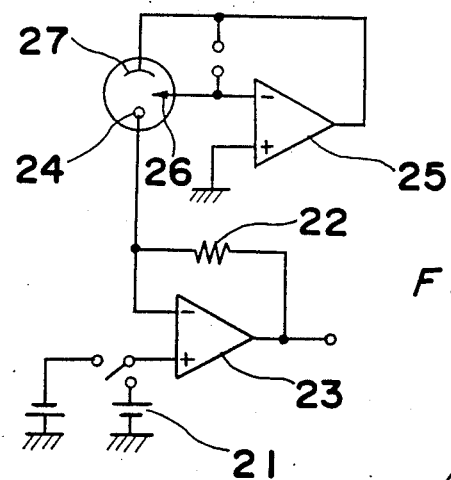
FIG. 7 is a circuit diagram of a control circuit adapted in a conventional biosensor (already referred to).

Before the description of the present invention proceeds, it is to be noted that like parts are designated by like reference numerals throughout the accompanying drawings.

Figure 2:
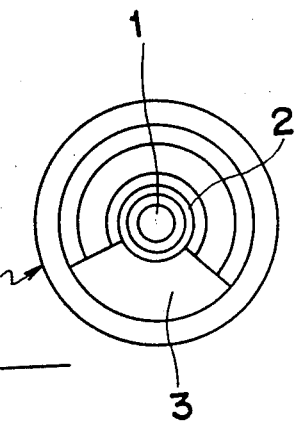
FIG. 2 is a top plane view of the body of FIG. 1.

Referring to FIGS. 1 to 3, there is shown a biosensor, in accordance with one preferred embodiment of the present invention, which comprises an enzyme electrode body 13 having a foundation electrode and an electric circuit for controlling the foundation electrode. The foundation electrode is provided on the surface of the enzyme electrode body 1 which is convex on one side and is comprised of a working electrode 1 made of Pt, a reference electrode 2 made of Ag, and a counter electrode 3 made of Ag, arranged in such a manner that the reference electrode 2 surrounds the larger part of the outer periphery of the working electrode 1 and the counter electrode 3 surrounds the working electrode 2, and such that a bias potential is supplied corresponding to the change of the potential of the counter electrode 3.

The biosensor is adapted to detect an object on the basis of an electrical signal produced between the working electrode which is secured with physiologically active material and, the counter electrode in the state where a predetermined normal bias voltage is supplied between the working electrode and the reference electrode.

The electric circuit is provided with an electrode refreshing arrangement which is arranged to apply to the electrodes a bias voltage having a polarity which is opposite that at the time of measurement, before starting the measurement, to refresh the electrodes. The electrode refreshing arrangement comprises a measurement direct current source 12 for supplying a first constant voltage between the reference electrode 2 and the working electrode 1 for the purpose of 15 measurement of the object, a refreshing direct current source 6 for supplying a second constant voltage between the working electrode 1 and the reference electrode 2 for the purpose of refreshing the working electrode 2 and a selecting means 5 which, when the measurement is carried out, selects the state where the constant voltage for the purpose of refreshing is supplied by the refreshing direct current source and the state where the constant voltage for the purpose of measurement is supplied by the measurement direct current source, alternately in this order.

The reference electrode 2 and the counter electrode 3 are respectively connected to an inverting input terminal 4a and an output terminal 4c of an operational amplifier 4. The operational amplifier 4 has its non-inverting input terminal 4b selectively connected to the direct current source 6 for refreshing or to ground 7, by a switch 5. An operational amplifier 8 for use in current-voltage conversion is provided to output a signal, with its inverting input terminal 8a connected to the working electrode 1. Moreover, a resistance 9 for use in current-voltage conversion is connected between an output terminal 8c and the inverting input terminal 8a of the operational amplifier 8, and at the same time, a diode 10 is connected between the inverting input terminal 8a and a non-inverting input terminal 8b of the operational amplifier 8, with an anode thereof positioned at the side of the inverting input terminal 8b. There is the direct current source 12 for measurement use connected between a non-inverting input terminal 11b of a buffer amplifier 11 and ground 7. An output terminal 11c of the buffer amplifier 11 is directly connected to an inverting input terminal 11a and is also connected to the non-inverting input terminal 8b of the operational amplifier 8. It is to be noted that the terminal voltage Vr of the direct current source 6 and the terminal voltage Vm of the direct current source 12 are set so as to establish $Vr \geq Vm$.

The surface of the enzyme electrode body 13 at the side where the above-described electrodes 1, 2 and 3 are provided is convex, and moreover, there are formed a transmissive film 14 which selects to pass through hydrogen peroxide, a fixed GOD film 15 which is secured glucose oxydase (hereinafter referred to as GOD) and a dispersion control film 16 made of cellophane in this order to cover the convex surface. It is to be noted here that each terminal 17 is connected to respective electrodes 1, 2 and 3 so as to take out a signal.

The operation of the sensor for detecting the glucose density having the above-described construction will be explained hereinbelow.

In order to measure the glucose density, first, the switch 5 is switched to connect the non-inverting input terminal 4b of the operational amplifier 4 with the refreshing direct current source 6, so that the constant voltage for refreshing is applied between the working electrode 1 and the reference electrode 2.

In the above condition, the refreshing direct current source 6 becomes series-connected to the measurement direct current source 12, and accordingly, the voltage equal to the terminal voltage difference $(Vr - Vm)$ between the direct current sources 6 and 12 is applied to the working electrode 1 as a reverse bias voltage, with respect to the reference electrode 2 as the standard. Since the surface potential of the reference electrode 2 is not changed, without influences by the change of the potential of the counter electrode 3 as shown in FIG. 4 with a real line of A, the surface potential of the working electrode 1 can be held constant.

Figure 5:
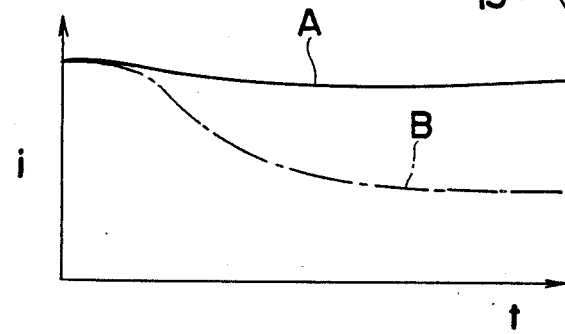
FIG. 5 is a graph showing a relationship between current and voltage of the biosensor of FIG. 1.

Accordingly, an almost constant refreshing current is supplied to the working electrode 1, as shown in FIG. 5 with a real line of A, and therefore the disturbance substance against the circulation of electricity can be effectively removed, restoring the activity of the working electrode 1.

Thereafter, when the switch 5 is switched, and the non-inverting input terminal 4b of the operational amplifier 4 and ground 7 are directly connected, the voltage equal to the terminal voltage Vm in the direct current source 12 is added to the working electrode 1 as a normal bias voltage, with respect to the standard reference electrode 2, so that the sensor is brought into the measurable condition.

In the condition as described above, if the solution of the object to be measured is dropped into the enzyme electrode, a signal corresponding to the glucose density is outputted in the following manner.

While the transmission of glucose in the solution of the object to be measured is restricted to some degrees by the dispersion control film 16, the solution is guided to the fixed GOD film 15 where the enzyme reaction expressed by [glucose+$O_2$+$H_2O^{GOD}$→glucon oxide+$H_2O_2$] takes place, as a result, $H_2O_2$ in the amount corresponding to the density of glucose present in the object to be measured is produced. Then, the produced $H_2O_2$, passing through the hydrogen peroxide transmission film 14, is led to the surface of the working electrode 1 which has been restored to have good activity. At this time, since the working electrode 1 not only has sufficient activity, but is supplied with the normal bias voltage, the oxidation reaction is performed on the surface of the working electrode 1 and, simultaneously with this, the current corresponding to the amount of the produced $H_2O_2$ flows in through the working electrode 1. The current is supplied to the inverting-input terminal 8a of the operational amplifier 8. Accordingly, a voltage signal which is obtained in a manner that the voltage signal in proportion to the above current is added to the offset voltage by the normal bias voltage can be obtained. In this case, the level of the voltage signal is higher than the stable level in the case after the lapse of a long period of time since the supply of electricity as the working electrode 1 is made sufficiently active, and accordingly the measurement resolution is high.

Thereafter, therefore, only the voltage signal proportional to the above current is extracted to the subjected to the primary differential calculus, and the peak value of the primary differential calculus is detected, so that highly accurate signal of the glucose density can be obtained, with necessary operations being carried out.

Although no description is made hereinabove as to the voltage for refreshing and the time period for voltage application, it is enough to achieve good refreshing effects that approximately 0–1.2 V may be added which allows to flow the current about ten times as large as the measurement current, and also the voltage application may be continued for 1–10 seconds or so.

It is to be noted here that the present invention is not restricted to the above-described embodiment. For example, the counter electrode 3 may be formed of Pt, Au or the like. Moreover, the constant voltage for the purpose of refreshment may be suitably selected in accordance with the kinds of electrodes. Further, the diode 8 in the aforementioned embodiment may be replaced with a switching transistor, or switching elements may be employed for the switch 5.

Figure 6:
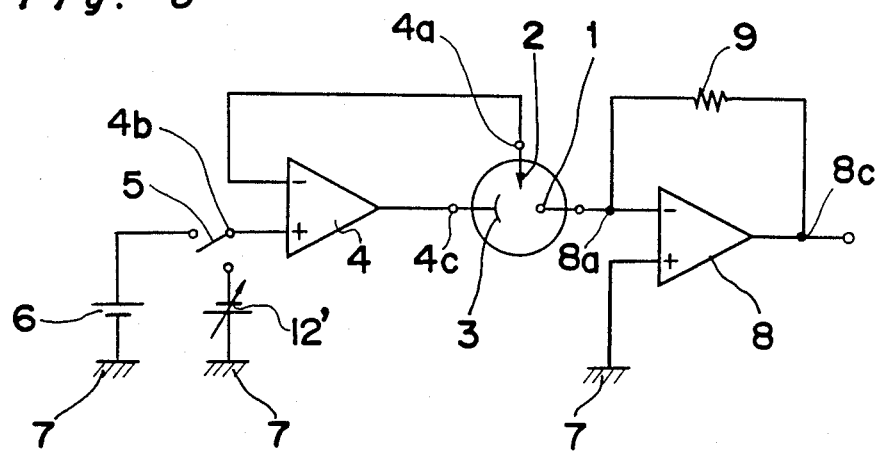
FIG. 6 is a view similar to FIG. 3, but showing a modification of the control circuit.

FIG. 6 shows a modification of a circuit diagram for controlling the foundation electrode as in the circuit diagram of FIG. 3. In the modification of FIG. 6, the buffer amplifier 11 and diode 10 of FIG. 3 are deleted with (−) input terminal of the operational amplifier 8 being connected directly to ground 7, and the measurement direct current source of FIG. 3 is replaced by a new measurement direct current source 12' of negative type which is connected in parallel with the refreshing direct current source 6 between the switch 5 and ground. The operation of the modification of FIG. 6 is almost the same as that of the embodiment of FIG. 3 except that the new measurement direct current source 12' supplies a negative current to the electrodes through the switch 5 and operational amplifier 4 for the purpose of measurement of the object.

As has been clearly described in the foregoing embodiment, according to the electrode refreshing arrangement of the present invention, a constant reverse bias is arranged to be supplied between the working electrode and the reference electrode of the biosensor so as to refresh the working electrode. Thereafter, while a constant normal bias voltage is supplied between the working electrode which is refreshed as above and the reference electrode, the density of the object is measured. Accordingly, the electrode refreshing arrangement of the present invention displays such an advantage that the measurement can be performed with high precision in a short period of time after the supply of electricity.

What is claimed is:

1. A biosensor comprising:
an enzyme electrode body;
a foundation electrode provided on the enzyme electrode body and including a working electrode, a counter electrode and a reference electrode;
an enzyme film provided on the surface of the foundation electrode and fixed with physiologically active material so that an electrical signal is generated in the foundation electrode on the basis of the result of the enzyme reaction to measure the density of an objective material, and an electrical circuit including:
a first operational amplifier having an inverting input and a non-inverting input and an output, said inverting input being connected to said reference electrode and said output being connected to said counter electrode;
a first constant voltage supplying means and a second constant voltage supplying means;
a switching means for selectively connecting said non-inverting input of said first operational amplifier to said first constant voltage supplying means and to ground;
a second operational amplifier having a non-inverting input and an inverting input and an output, said inverting input being connected to said working electrode and said non-inverting input being connected to said second constant voltage supplying means;
a resistance means connected between said inverting input of said second operational amplifier and said output of said second operational amplifier;
a unipolar current carrying device connected between said inverting and non-inverting inputs of said second operational amplifier and arranged to conduct current only if a potential at said inverting input of said second operational amplifier is greater than a potential at said non-inverting input of said second operational amplifier;
wherein said switching means, when selectively connecting said non-inverting input of said first operational amplifier to said first constant voltage supplying means, places the biosensor in a refresh state for refreshing said working electrode while keeping a voltage drop in a vicinity of a surface of said working electrode constant and wherein when said selecting means connects said non-inverting input of said first operational amplifier to ground, the biosensor is placed in a measuring state such that a signal present at said output of said second operational amplifier is proportional to said electrical signal generated in said foundation electrode.

2. A biosensor as recited in claim 1, wherein said second constant voltage supplying means comprises a third operational amplifier having an inverting input and a non-inverting input and an output and a constant voltage source, said constant voltage source being connected between said non-inverting input of said third operational amplifier and ground and said inverting input of said third operational amplifier being connected to said output of said third operational amplifier, wherein said output of said third operational amplifier is the output of said second constant voltage supplying means.

3. A biosensor as recited in claim 1 or 2, wherein said unipolar current carrying device comprises a diode.

4. A biosensor as recited in claims 1 or 2, wherein said reference electrode is made of silver.

5. A biosensor comprising:
an enzyme electrode body;
a foundation electrode provided on the enzyme electrode body and including a working electrode, a counter electrode and a reference electrode;
an enzyme film provided on the surface of the foundation electrode and fixed with physiologically active material so that an electrical signal is generated in the foundation electrode on the basis of the result of the enzyme reaction to measure the concentration of an objective material, and an electrical circuit including:
a first amplifier having a pair of inputs and an output, one of said inputs being connected to said reference electrode while said output is connected to said counter electrode;
a first constant voltage supplying means and a second constant voltage supply means;
a switching means for selectively connecting the other of said inputs of said first amplifier to said first constant voltage supplying means and to ground;
a second amplifier having a pair of inputs, one of which being connected to said working electrode while the other of which is connected to said second constant voltage supplying means;
a unipolar current carrying device connected between said inputs of said second amplifier and arranged to conduct current only if a potential at one of said inputs of said second amplifier is greater than a potential at the other of said inputs of said second amplifier;
wherein said switching means, when selectively connecting said other input of said first amplifier to said first constant voltage supplying means, places the biosensor in a refresh stat for refreshing said working electrode while keeping a voltage drop in the vicinity of a surface of said working electrode constant and wherein when said selecting means connects said other input of said first amplifier to ground, the biosensor is placed on a measuring state such that a signal present at said output of said second amplifier is proportional to said electrical signal generated in said foundation electrode.

6. A biosensor as recited in claim 5, wherein said second constant voltage supplying means comprises a third amplifier having a pair of inputs and an output and a constant voltage source, said constant voltage source being connected between one of said pair of inputs of said third amplifier and ground and the second of said pair of inputs of said third amplifier being connected to said output of said third amplifier, wherein said output of said third amplifier is the output of said second constant voltage supplying means.

7. A biosensor as recited in claims 5 or 6, wherein said unipolar current carrying device comprises a diode.

8. A biosensor as recited in claims 5 or 6, wherein said reference electrode is made of silver.

* * * * *